United States Patent
Yuasa et al.

(10) Patent No.: US 12,114,865 B2
(45) Date of Patent: Oct. 15, 2024

(54) CLIP FOR ENDOSCOPE

(71) Applicant: OLYMPUS MEDICAL SYSTEMS CORP., Tokyo (JP)

(72) Inventors: Masaru Yuasa, Hachioji (JP); Yoshitsugu Uekusa, Tachikawa (JP); Tatsunori Tsuneto, Hino (JP); Shinya Ansai, Koganei (JP); Shogo Shindo, Koganei (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 17/498,062

(22) Filed: Oct. 11, 2021

(65) Prior Publication Data
US 2022/0117604 A1   Apr. 21, 2022

Related U.S. Application Data

(60) Provisional application No. 63/092,981, filed on Oct. 16, 2020.

(51) Int. Cl.
*A61B 17/122* (2006.01)
*A61B 17/00* (2006.01)
(Continued)

(52) U.S. Cl.
CPC ............ *A61B 17/122* (2013.01); *A61B 17/10* (2013.01); *A61B 17/1285* (2013.01);
(Continued)

(58) Field of Classification Search
CPC . A61B 17/122; A61B 17/083; A61B 17/1222; A61B 17/128; A61B 17/1225;
(Continued)

(56) References Cited

U.S. PATENT DOCUMENTS

| 5,409,498 A | 4/1995 | Braddock et al. |
| 5,620,452 A * | 4/1997 | Yoon .................... A61B 17/122 |
| | | 606/151 |

(Continued)

FOREIGN PATENT DOCUMENTS

| CN | 210077721 U | 2/2020 |
| EP | 1872730 A1 | 1/2008 |

(Continued)

OTHER PUBLICATIONS

Office Action (OA-1) dated Sep. 6, 2022, issued in corresponding Japanese Patent Application No. 2021-165768.
(Continued)

*Primary Examiner* — Shaun L David
*Assistant Examiner* — Rachael L Geiger
(74) *Attorney, Agent, or Firm* — Morgan, Lewis & Bockius LLP

(57) ABSTRACT

A clip for gripping tissue can having a first arm with a first claw at a distal end of the first arm, and second arm, with a second claw at a distal end of the second arm, in which the first arm and second arm are configured to move in a direction toward each other to close the clip. The clips include one or more anchors on the arms of the clip which protrude in a direction other than the direction that the first arm and second arm are configured to move toward each other to close the clip. Such anchors can more readily attach to tissue of a patient upon contact than clips without an anchor.

19 Claims, 23 Drawing Sheets

(51) Int. Cl.
  *A61B 17/08* (2006.01)
  *A61B 17/10* (2006.01)
  *A61B 17/128* (2006.01)

(52) U.S. Cl.
  CPC .............. *A61B 2017/00336* (2013.01); *A61B 2017/0034* (2013.01); *A61B 2017/00367* (2013.01); *A61B 2017/00831* (2013.01); *A61B 17/083* (2013.01)

(58) Field of Classification Search
  CPC ............ A61B 17/1227; A61B 17/1285; A61B 2017/00336; A61B 2017/0034; A61B 2017/00584; A61B 2017/2931; A61B 2017/2937
  See application file for complete search history.

(56) References Cited

U.S. PATENT DOCUMENTS

| | | | |
|---|---|---|---|
| 5,904,647 | A | 5/1999 | Ouchi |
| 8,162,959 | B2 | 4/2012 | Cohen et al. |
| 8,480,685 | B2 | 7/2013 | Kimura et al. |
| 9,949,740 | B2 | 4/2018 | Satake et al. |
| 10,624,642 | B2 | 4/2020 | Randhawa |
| 10,786,254 | B2 | 9/2020 | Wells et al. |
| 2002/0045909 | A1 | 4/2002 | Kimura et al. |
| 2002/0138086 | A1* | 9/2002 | Sixto, Jr. ............ A61B 17/0644 606/151 |
| 2002/0165560 | A1 | 11/2002 | Danitz et al. |
| 2002/0198541 | A1 | 12/2002 | Smith et al. |
| 2003/0069592 | A1 | 4/2003 | Adams et al. |
| 2004/0176784 | A1 | 9/2004 | Okada |
| 2005/0059985 | A1 | 3/2005 | Kimura |
| 2005/0124912 | A1 | 6/2005 | Griego et al. |
| 2005/0143767 | A1 | 6/2005 | Kimura et al. |
| 2006/0271066 | A1 | 11/2006 | Kimura et al. |
| 2006/0276775 | A1 | 12/2006 | Rosenberg et al. |
| 2008/0114377 | A1 | 5/2008 | Shibata et al. |
| 2008/0249566 | A1 | 10/2008 | Harris et al. |
| 2009/0318937 | A1* | 12/2009 | Matsuoka .......... A61B 17/1285 606/151 |
| 2010/0152753 | A1 | 6/2010 | Menn et al. |
| 2011/0172682 | A1 | 7/2011 | Brady et al. |
| 2011/0208211 | A1 | 8/2011 | Whitfield et al. |
| 2011/0319710 | A1 | 12/2011 | Phillips-Hungerford et al. |
| 2012/0029534 | A1 | 2/2012 | Whitfield et al. |
| 2012/0150301 | A1 | 6/2012 | Gamache et al. |
| 2013/0023925 | A1 | 1/2013 | Mueller |
| 2013/0158566 | A1 | 6/2013 | Harris et al. |
| 2013/0310857 | A1* | 11/2013 | Iceman ............ A61B 17/00234 606/151 |
| 2015/0133969 | A1* | 5/2015 | Gupta .................... A61B 17/10 606/151 |
| 2015/0230799 | A1 | 8/2015 | Satake et al. |
| 2017/0340443 | A1 | 11/2017 | Stearns et al. |
| 2019/0150929 | A1* | 5/2019 | Gregan .............. A61B 17/1285 |
| 2019/0321047 | A1* | 10/2019 | Thomas ............... A61B 17/122 |
| 2020/0113616 | A1 | 4/2020 | Honda |
| 2020/0205836 | A1* | 7/2020 | Uesaka ............. A61B 17/1285 |
| 2021/0106335 | A1* | 4/2021 | Sugitani ................ A61B 90/39 |

FOREIGN PATENT DOCUMENTS

| | | |
|---|---|---|
| EP | 2127606 A1 | 12/2009 |
| JP | 06-209948 A | 8/1994 |
| JP | 2004-121485 A | 4/2004 |
| JP | 2004-527312 A | 9/2004 |
| JP | 2005-058626 A | 3/2005 |
| JP | 2006-158668 A | 6/2006 |
| JP | 2007-097664 A | 4/2007 |
| JP | 2007-136128 A | 6/2007 |
| JP | 2008-119068 A | 5/2008 |
| JP | 2010-213990 A | 9/2010 |
| JP | 2011-172931 A | 9/2011 |
| JP | 2012-030070 A | 2/2012 |
| JP | 2012-200518 A | 10/2012 |
| JP | 2013-255756 A | 12/2013 |
| JP | 2015-008858 A | 1/2015 |
| JP | 2016-123805 A | 7/2016 |
| JP | 2017-192513 A | 10/2017 |
| JP | 2018-061672 A | 4/2018 |
| WO | 00/76404 A2 | 12/2000 |
| WO | 2002/087421 A2 | 11/2002 |
| WO | 2004/008975 A1 | 1/2004 |
| WO | 2012/039163 A1 | 3/2012 |
| WO | 2019/099698 A1 | 5/2019 |
| WO | 2019/172318 A1 | 9/2019 |
| WO | 2019/189864 A1 | 10/2019 |
| WO | 2019/207585 A1 | 10/2019 |
| WO | 2020/136906 A1 | 7/2020 |
| WO | 2020/189666 A1 | 9/2020 |

OTHER PUBLICATIONS

Office Action (OA-2) dated Sep. 6, 2022, issued in corresponding Japanese Patent Application No. 2021-165771.
Extended European Search Report (OA-1) dated Feb. 11, 2022, issued in corresponding European Patent Application No. 21201423.7.
Extended European Search Report (OA-2) dated Mar. 11, 2022, issued in corresponding European Patent Application No. 21201671.1.
Office Action dated Feb. 22, 2023, issued in related U.S. Appl. No. 17/498,064.
International Search Report dated Jan. 11, 2022, issued in corresponding International Search Report PCT/JP2021/038151.
Office Action issued on Jun. 27, 2023 in U.S. Appl. No. 17/498,064.
Office Action dated Nov. 15, 2023, issued in Chinese Patent Application No. 202111181510.X.
Office Action dated Apr. 2, 2024, issued in Japanese Patent Application No. 2021-165771.
Third Party Observations dated Apr. 30, 2024, issued in European Patent Application No. 21201423.7.
Office Action dated May 28, 2024, issued in corresponding Chinese Patent Application No. 202111181510.X.
Office Action dated Jul. 17, 2024, issued in corresponding European Patent Application No. 21201423.7.
Office Action issued in U.S. Appl. No. 18/411,596 dated Aug. 8, 2024.

* cited by examiner

During scope insertion

When using clips

At the time of release

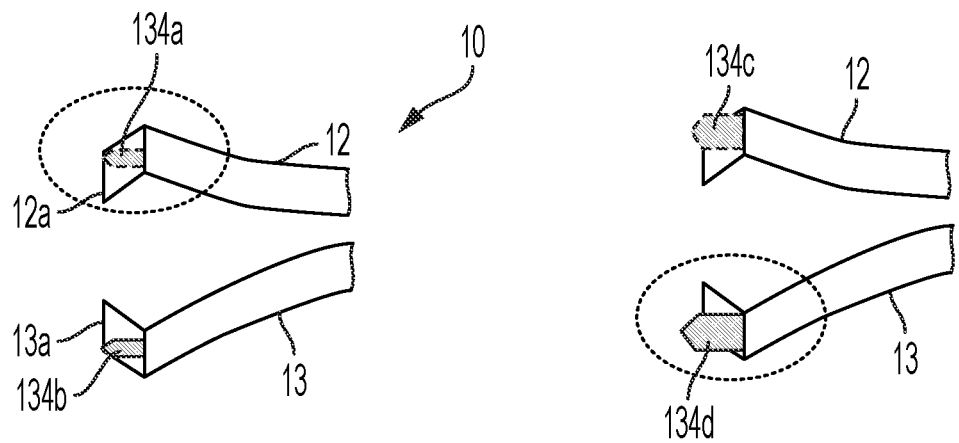
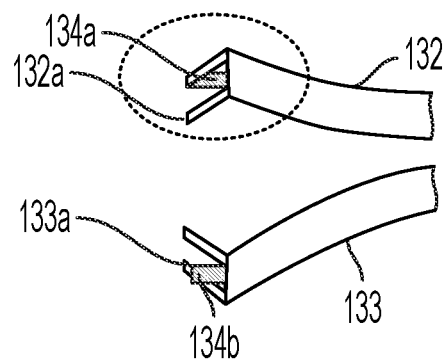
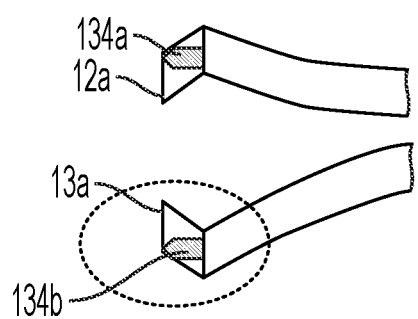
FIG. 13A          FIG. 13B

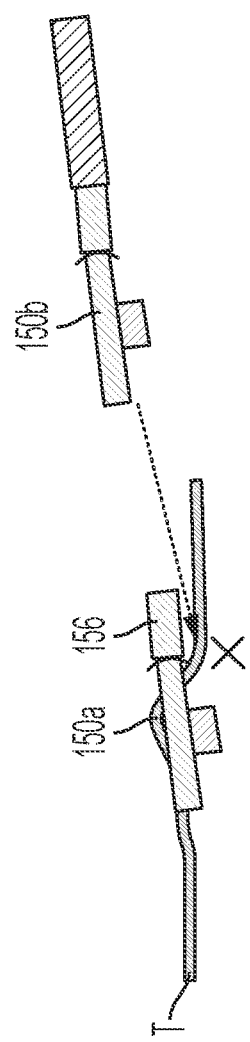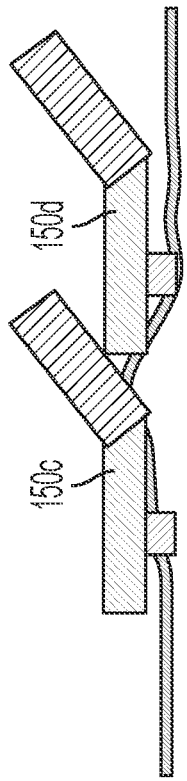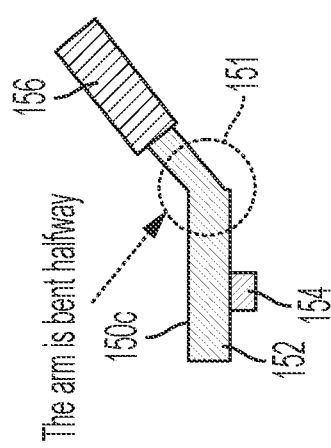

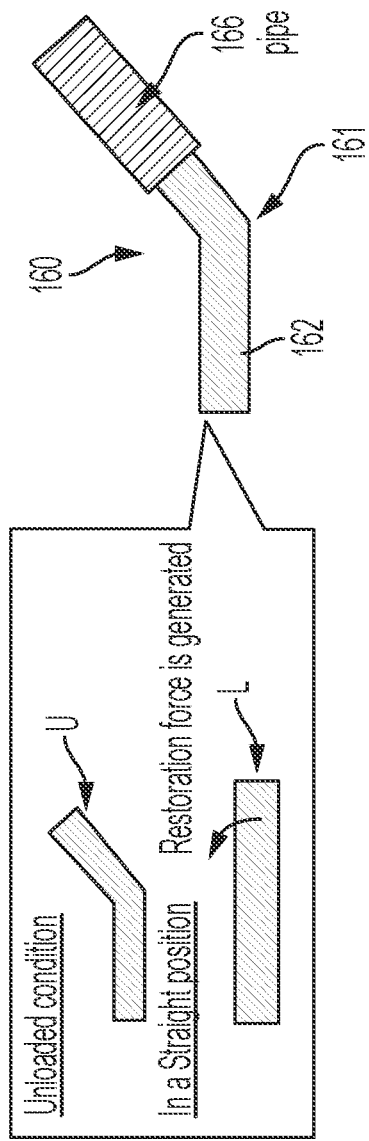
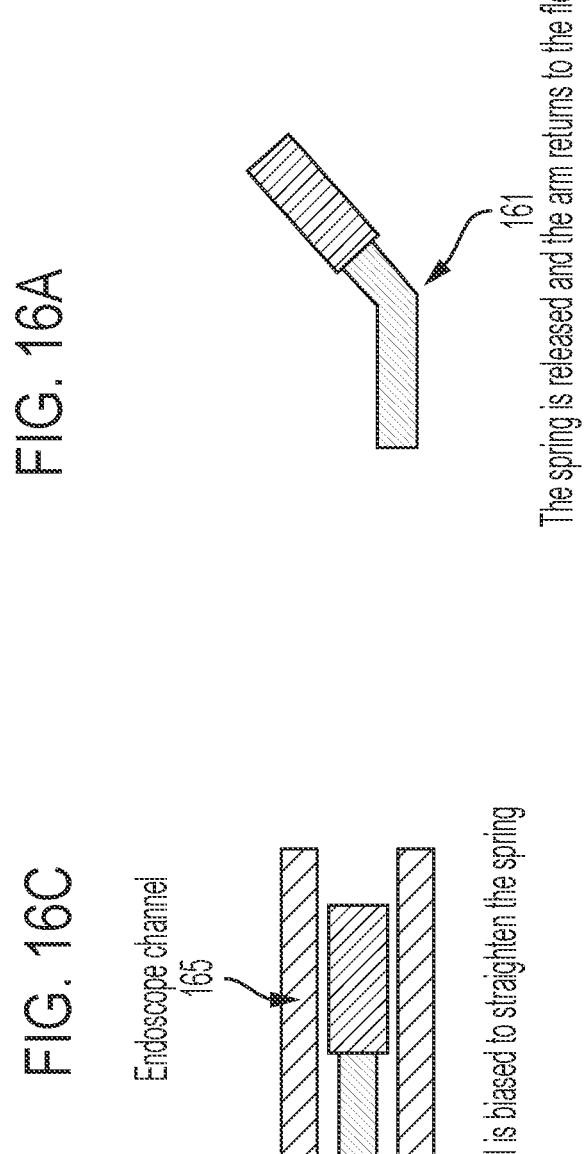
FIG. 16A
FIG. 16B
The spring is released and the arm returns to the flexed state
FIG. 16C

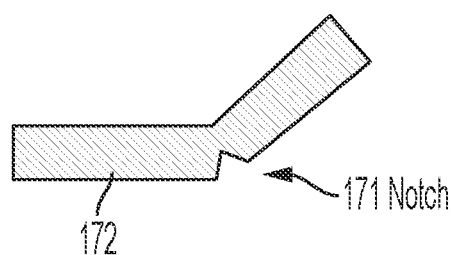
FIG. 17A
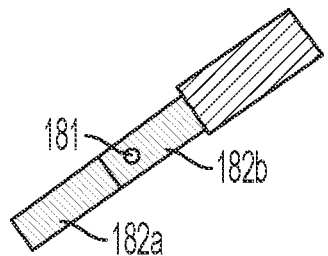  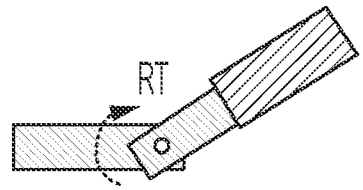
FIG. 18A        FIG. 18B

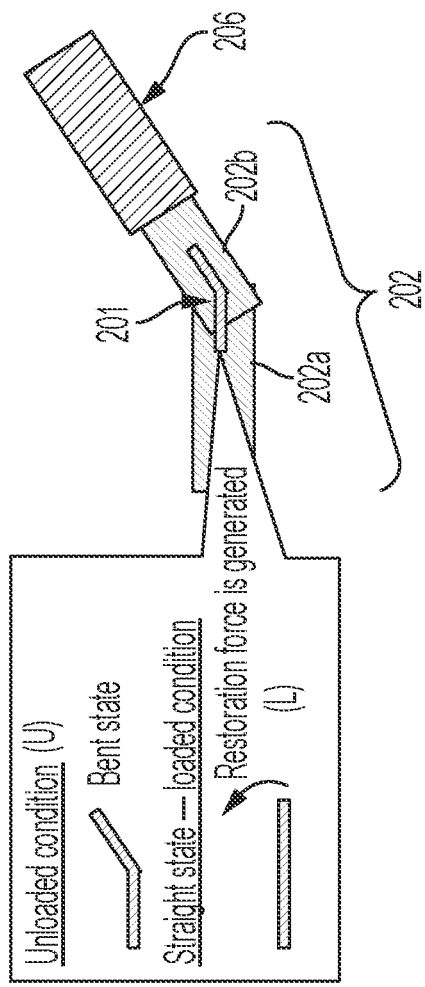
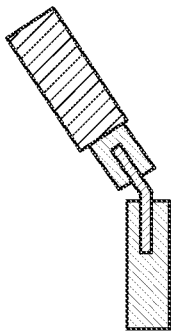
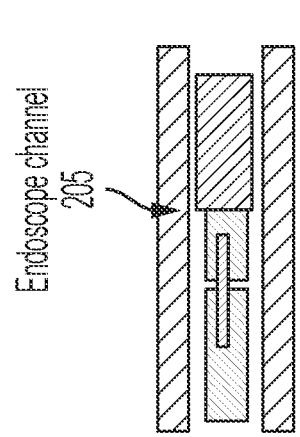
FIG. 20A
FIG. 20B
FIG. 20C The channel is biased to straighten the spring
FIG. 20D The spring is released and the arm returns to the flexed state

CLIP FOR ENDOSCOPE

CROSS-REFERENCE TO RELATED APPLICATION

This application claims the benefit of U.S. Provisional Application No. 63/092,981 filed 16 Oct. 2020, the entire disclosure of which is hereby incorporated by reference herein.

TECHNICAL FIELD

The present invention relates to clips configured to grasp tissue of a patient in a surgical procedure and can be used with surgical tools such as endoscopes.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Endoscopic clips, i.e., endoclips, are surgical tools used with endoscopes that can grasp tissue within a human body. Endoclips have found use in therapeutic procedures such as to prevent tissue bleeding, closing perforations, and other surgical procedures. There are many types of endoclips differing in shape and/or size, which can be administered using single use and reloadable systems, and may or may not open and close to facilitate placement of the clip in the body.

For example, JP 2015008858 discloses an endoscope clip for grasping body tissue that includes protrusions on inner surfaces of arm plates of the clip. The protrusions are directed inward to face each other and are designed to facilitate holding tissue between the arms of the clip when the clip is closed.

However, a continuing need exists for clips configured to grasp tissue of a patient in a surgical procedure and can be used with surgical tools such as endoscopes.

SUMMARY OF THE DISCLOSURE

An advantage of the present invention is a clip that includes an anchor which can more readily attach to tissue of a patient upon contact with the tissue than clips without an anchor. Clips of the present disclosure can more readily facilitate grasping tissue when the clip approaches such tissue at an angles less than perpendicular to the tissue, for example.

These and other advantages are satisfied, at least in part, by a clip for gripping tissue having a first arm, with a first claw at a distal end of the first arm, and second arm, with a second claw at a distal end of the second arm. The first arm and second arm are configured to move in a direction toward each other to close the clip. In some embodiments, the first claw and second claw face each other. In further embodiments, the first and second arms can move in a reciprocal direction toward and away from each other to close and open the clip. In other embodiments, the first arm and second arm are configured to move in a direction toward each other to close the clip and once the arms close, the clip can be locked from opening.

Advantageously, the clip includes one or more anchors such as a first anchor on the first arm. Optionally, the clip can also include a second anchor such as on the second arm. The first anchor can protrude from the first arm in a direction other than the direction that the first arm and second arm are configured to move toward each other to close the clip. And, when present, the second anchor can protrude from the second arm in a direction other than the direction that the first arm and second arm are configured to move toward each other to close the clip. In several embodiments, the clip includes the first anchor and the second anchor.

Additional embodiments of the present disclosure include one or more of the following features individually or combined. For example, the clips of the present disclosure can be assembled with a pressing tube, which can be connected to a sheath. The clip can also be connected to a wire directly or through a connection member. In some embodiments, the assembly can include a cover to shield the first anchor and optional second anchor when the clip is retracted in a pressing tube. In other embodiments, the first and optional second anchor can protrude through slits in the arms. In still further embodiments, the first and optional second anchor can protrude from the arms in a direction that is orthogonal to a plane defined by the first and second arm. In other embodiments, the anchors can be configured to rotate toward a plane defined by the first and second arm. In some embodiments, of the first arm and the second arm are configured to bend.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein:

FIGS. 13A and 13B schematically illustrate clips with claws that have a gap, or in which a width of a claw is greater or less than a width of an anchor so that the anchors can be more readily observed when the clip is in use in accordance with aspects of the present disclosure.

FIGS. 15A and 15B schematically illustrate a side view of a clip configured to be released from a surgical tool after the clip is attached to tissue of a patent and including a bending member on the arms of the clip in accordance with aspects of the present disclosure FIGS. 16A and 16B schematically illustrate a side view of a clip configured to include a bending member on the arms of the clip in accordance with aspects of the present disclosure.

FIG. 16C is an enlarged view of the clip arms of FIG. 16A.

FIG. 17A schematically illustrates a side view of a clip configured to include a bending member on the arms of the clip and a notch in accordance with aspects of the present disclosure.

FIGS. 18A and 18B schematically illustrate a side view of a clip with arms having two part articulated together through joints in accordance with aspects of the present disclosure.

FIGS. 20A, 20B, 20C, 20D schematically illustrate a side view of another embodiment of a clip with arms having two part articulated together through joints in accordance with aspects of the present disclosure.

Figure 1A:
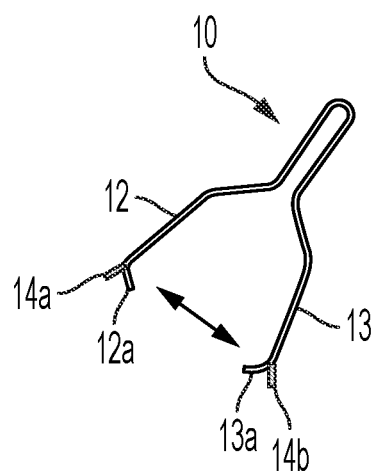
FIGS. 1A, 1B, 1C and 1D schematically illustrate a clip with anchors protruding from an outer surface of the first arm and an outer surface of the second arm. The anchors are shown in this example as protruding from the respective arms in a direction that diverges from the reciprocal direction of the first and second arms that opens and closes the clip.
Figure 1B:
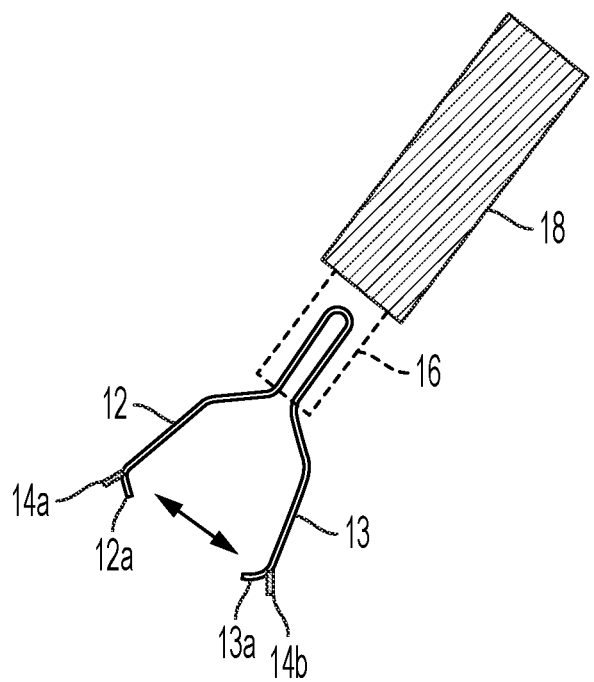

Throughout all of the drawings, dimensions of respective constituent elements are appropriately adjusted for clarity. For ease of viewing, in some instances only some of the named features in the figures are labeled with reference numeral.

DETAILED DESCRIPTION OF THE DISCLOSURE

Clips of the present disclosure are useful in therapeutic procedures of a patient such as to prevent tissue bleeding, closing perforations and hemostasis, and suture contraction of the inner wound, marking lesions and traction (mucosal elevation) and other surgical procedures. The term "patient," as used herein, comprises any and all organisms and includes the term "subject." A patient can be a human or an animal.

Generally clips for grabbing tissue of a patient are actuated by a clip operation tool. Such a tool actuates the clip by an operational wire typically housed in a flexible tube in which the operational wire can advance and retract longitudinally in the flexible tube by operating an handle of the tool. References herein to the term "distal" are to a direction away from the operating handle, while references to the term "proximal" are to a direction towards the operating handle. Clip operation tools such as those described in U.S. Pat. Nos. 8,480,685 and 9,949,740 can be used with the clips of the present disclosure and the disclosures of each are incorporated in full herein by reference.

Various embodiments and aspects of a clip according to the present disclosure will be described with references to FIGS. 1 through 20.

As shown in FIGS. 1A-1D, a clip 10 for gripping biological tissue of a patient has a first arm 12, which has a first claw 12a at a distal end of the first arm 12, and a second arm 13, which has a second claw 13a at a distal end of the second arm 13. As further illustrated, first claw 12a and second claw 13a face each other and first arm 12 and second arm 13 are configured to move in a reciprocal direction (R) toward and away from each other to close and open the clip. The first and second claws can be on the same or approximately the same plane such that when the arms close, the claws contact each other.

Clips of the present disclosure advantageously include one or more anchors protruding from the first arm and/or the second arm. An anchor as used herein includes a structure that can attach to tissue of a patient upon contact with minimal force and can include, for example, a protrusion, hook, barb, spike, etc. The one or more anchors protrude from their respective arms in a direction other than the direction that the first and second arms are configured to move toward each other to close the clip. For example, the anchor can protrude in a direction divergent from a claw or in a direction that is orthogonal to a plane defined by the first and second arm (in a vertical direction relative to an arm) or protruding at any other direction other than the direction the first and second arms are configured to move toward each other to close the clip.

Figure 1C:
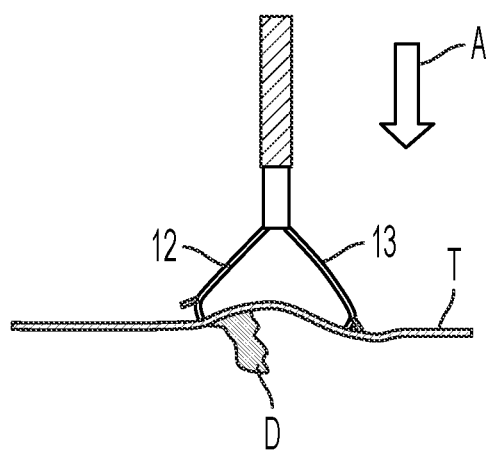
Figure 1D:
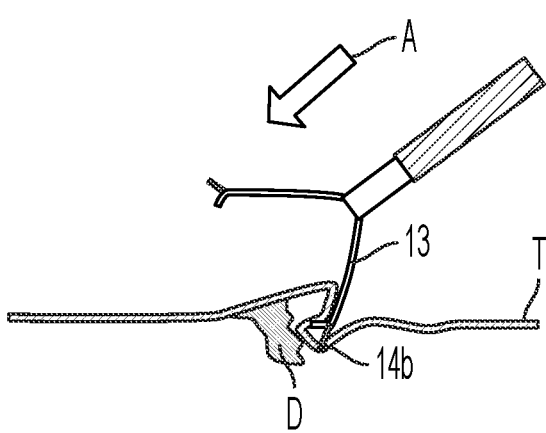

As further illustrated by FIGS. 1A-1D, first arm 12 includes a first anchor 14*a* on an outer surface of first arm 12 protruding in a direction divergent from first claw 12*a* and a second arm 13 includes a second anchor 14*b* on an outer surface thereon protruding in a direction divergent from second claw 13*a*. Clip 10 can deploy from within a pipe (also referred to herein as a pressing tube) 16 which can be coupled to a flexible tube 18. During operation, arms 12 and 13, which are biased toward an open, tissue receiving configuration as shown in FIGS. 1C and 1D, can be closed by actuating an operational wire (not shown) coupled to the clip to slidably move the clip proximally and distally in the pipe. The operational wire can advance and retract longitudinally in the flexible tube (not shown) by operating a handle of the tool (not shown). Slidably moving the clip distally and proximally opens and closes the clip by moving the arms and claws toward and away from each other. In some embodiments, once the clip is retracted in a pressing tube, the clip can be locked from opening.

As illustrated in FIGS. 1C-1D, an advantage of clips of the present disclosure is that they can attach to tissue even when the approach (A) of the clip is not perpendicular to the tissue, e.g. FIG. 1C illustrates a perpendicular approach while FIG. 1D illustrates a tangential approach. During a non-perpendicular approach anchor (14*b*) on arm 13 can catch tissue (T) near a defect (D). When closing the clip after the anchor catches tissue, the claw and arm can elevate the tissue so that the claws of the arms can more readily grasp the tissue. In addition, after an anchor catches tissue, the clip can be rotated to further grasp the tissue in the claw of the arm with the anchor attached to the issue. Advantageously, one or more anchors on outer surfaces of arms of clips of the present disclosure can prevent the distal end of an arm of a clip from slipping during a tangential approach to tissue (FIG. 1D).

Figure 2A:
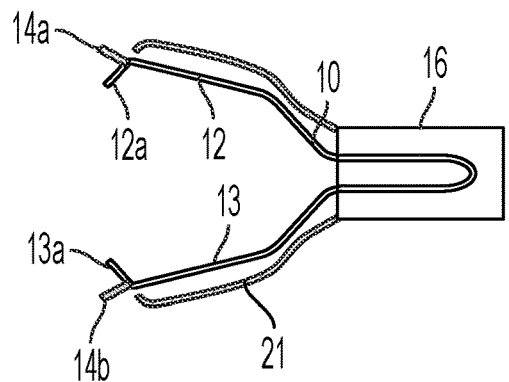
FIGS. 2A, 2B, 2C, 2D and 2E schematically illustrate a clip with anchors in which the anchors can be shielded by a cover connected to components of a clip device in accordance with aspects of the present disclosure.
Figure 2B:
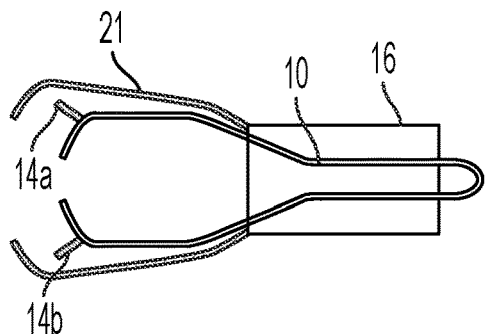

FIGS. 2A through 6B illustrate different aspects of clips of the present disclosure and different ways to mitigate contact of the anchors with other parts of a clip tool or endoscope. For example, FIGS. 2A-2E show a cover that can shield anchors of the clip. In FIGS. 2A-2B a cover 21 is attached to pressing tube (pipe) 16 and extending distally from pressing tube 16. Clip 10 can close (FIG. 2B) by slidably retracting in pressing tube 16. The cover can extend sufficiently distally to shield one or more anchors on outer surfaces of the arms when the clip is retracted in the pressing tube. As shown in FIG. 2B, cover 21 extends distally sufficiently to shield anchors 14*a* and 14*b* when clip 10 is retracted in pressing tube 16.

Figure 2C:
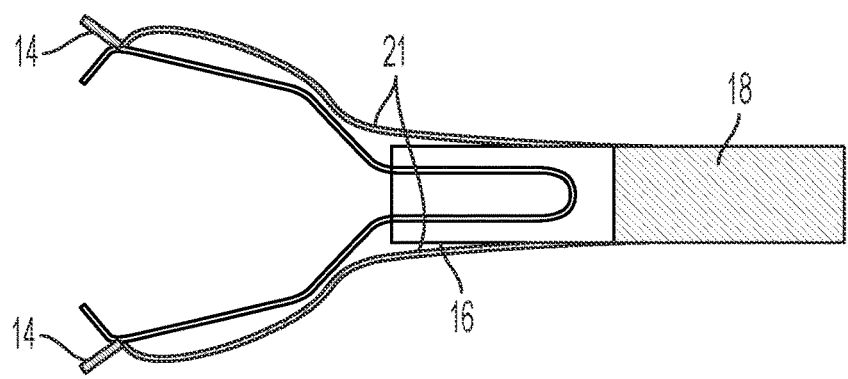
Figure 2D:
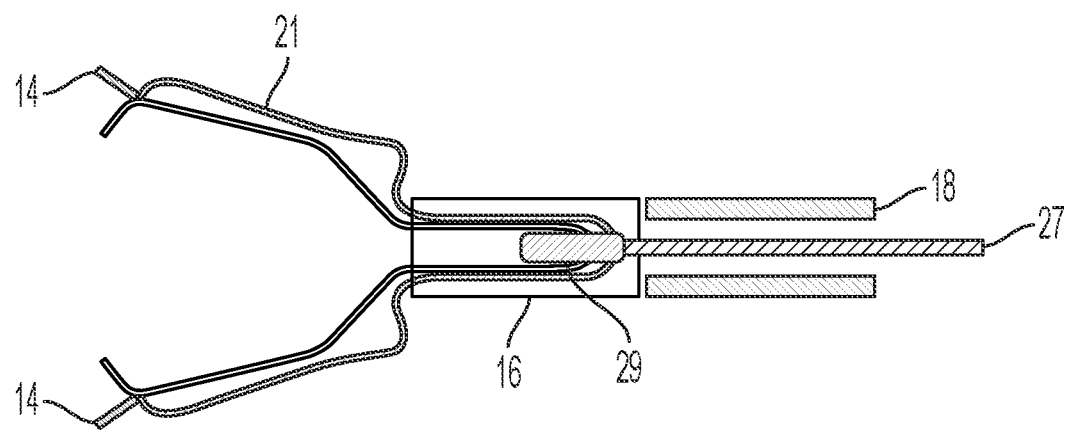
Figure 2E:
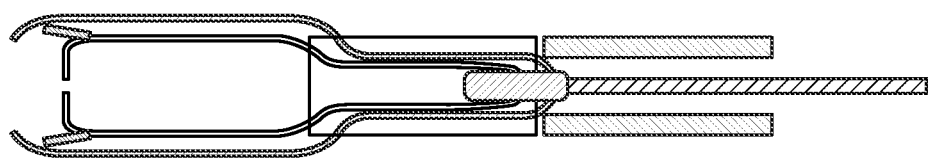

FIGS. 2C-2E illustrate different attachment locations for a cover that can shield anchors of the clip. For example, FIG. 2C shows cover 21 attached to sheath 18. FIGS. 2D-2E show how cover 21 can be attached to a connection member 29 or wire 27. FIG. 2D shows the clip in an open state with the anchors 14 exposed and FIG. 2E shows the clip in a closed state with the anchors shielded by cover 21. Irrespective of the location of attachment, the cover extends sufficiently distally to shield the anchors when the clip is retracted in the pressing tube. Cover 21 can be made of a plastic or other elastic material or a metal and can be attached by an adhesive or weld.

Figure 3A:
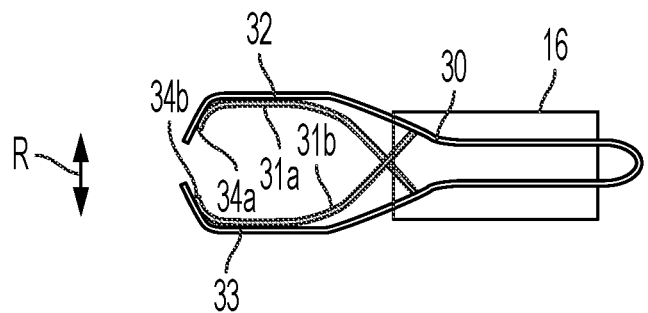
FIGS. 3A and 3B schematically illustrate flexible anchors that can protrude through slits in arms of a clip after the clip is opened in accordance with aspects of the present disclosure.
Figure 3B:
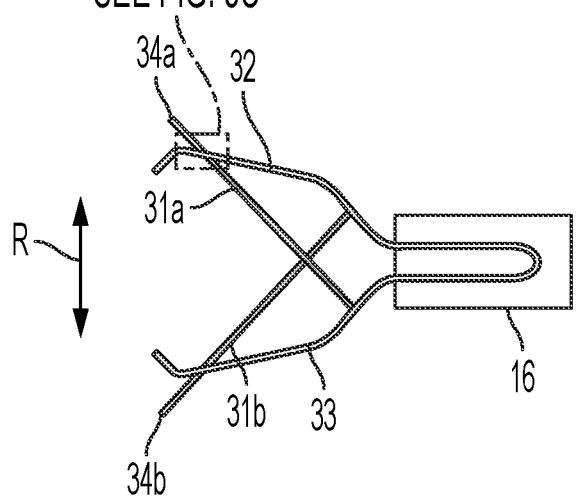
Figure 3C:
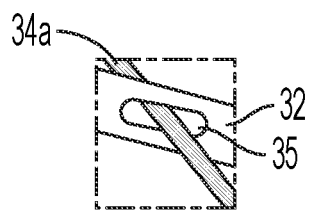
FIG. 3C is an enlarged view of an arm of a clip of FIG. 3B.

FIGS. 3A-3C and 4A-4C show flexible anchors that can protrude through slits in arms of a clip after the clip is opened. As illustrated in FIG. 3A, anchors 34*a* and 34*b* can be shielded by inner surfaces of first arm 32 and second arm 33 of clip 30 when the clip is in the closed state (FIG. 3A). The anchors 34*a* and 34*b* are connected to clip 30 by flexible members 31*a* and 31*b*, respectively. When clip 30 is in an opened state as illustrated in FIGS. 3B and 3C, anchor 34*a* protrudes through slit 35 in first arm 32 of clip 30. Anchor 34*b* similarly protrudes through a slit in second arm 33 when clip 30 is in an open state, which is not illustrated for convenience. In this way, the anchors can be shielded prior to deploying the clip, such as deploying clip 30 from pressing tube 16.

Figure 4A:
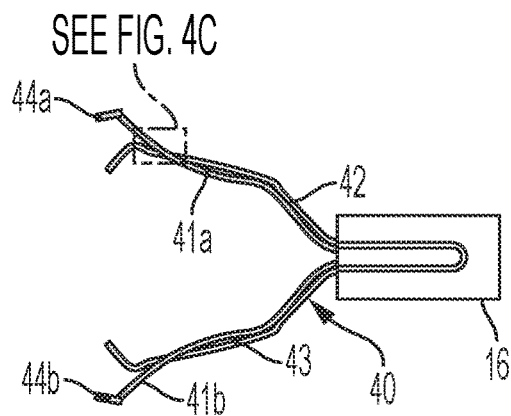
FIGS. 4A and 4B schematically illustrate flexible anchors that can protrude through slits in arms of a clip after the clip is opened in accordance with aspects of the present disclosure.
Figure 4B:
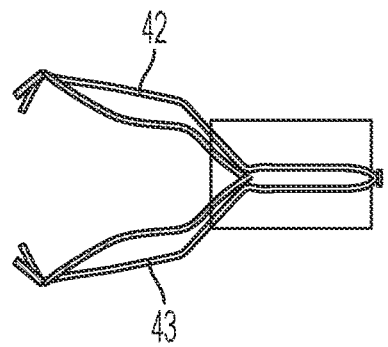
Figure 4C:
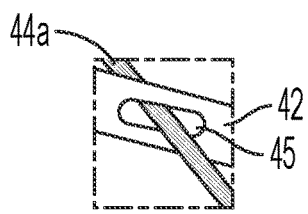
FIG. 4C is an enlarged view of an arm of a clip of FIG. 4B.

In separate embodiments, FIGS. 4A-4H show flexible anchors that can protrude through slits in arms of a clip after the clip is opened. In particular, anchors 44*a* and 44*b* can be retracted toward first and second arms 42 and 43, respectively, when the clip 40 moves toward a closed state (FIG. 4B-4C). The anchors 44*a* and 44*b* are connected to clip 40 by flexible members 41*a* and 41*b*, respectively. When clip 40 is in an opened state as illustrated in FIG. 4A, anchor 44*a* protrudes through slit 45 in first arm 42 of clip 40 by flexible member 41*a*. Anchor 44*b* similarly protrudes through a slit in second arm 43 when clip 40 is in an open state, which is not illustrated for convenience. In this way, the anchors can be brought toward the arms of the clip when the clip is retracted in pressing tube 16.

Figure 4D:
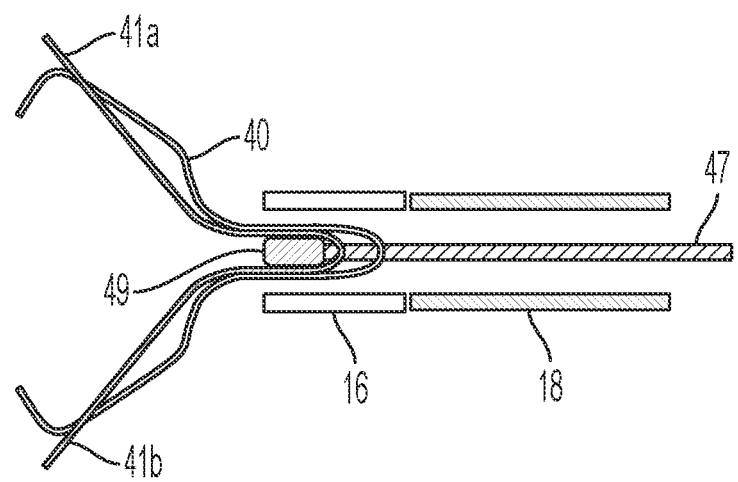
FIGS. 4D, 4E, 4F, 4G and 4H schematically illustrate other flexible anchors that can protrude through slits in arms of a clip after the clip is opened in accordance with aspects of the present disclosure.
Figure 4E:
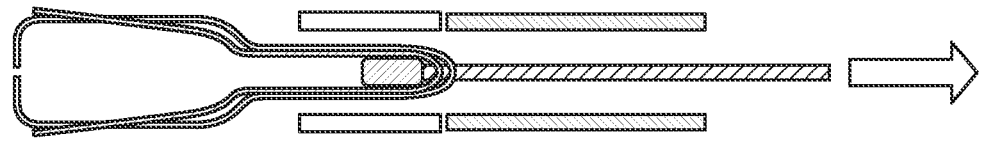
Figure 4F:
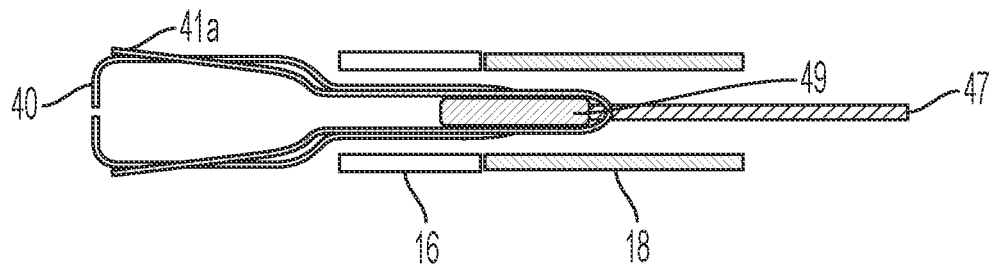
Figure 4G:
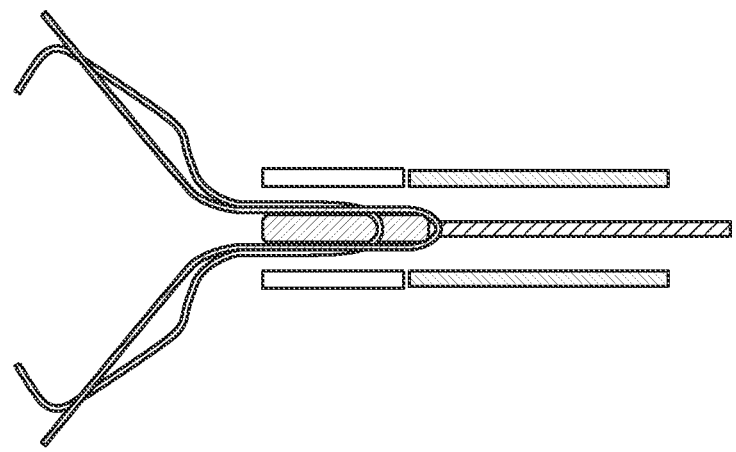
Figure 4H:
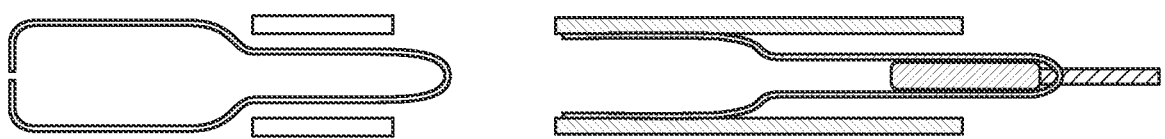

As further illustrated in FIGS. 4D-4H, clips and the flexible members can be in a closed state when inserted in a tool such as an endoscope (FIGS. 4E and 4F). Since the clip arms and flexible members are bias toward an open state, the clip arms and flexible members open in an operation of exiting a channel of the tool (FIGS. 4D and 4G). In operation, a handle (not shown) connected to a proximal end of wire (not shown) operates the wire (47) to retract the clip (40) in a pressing pipe (16) to close the clip arms. Certain clip devices can include a connection member (49) to engage and release a pressing tube from the sheath (18) (FIG. 4H). Such devices include a connection member to engage and disengage a distal end of the clip from the wire. In addition, the connection member can include internal engaging and disengaging elements. The flexible members can be connected to the wire or connection member and retracted in the pressing tube (FIG. 4H).

Figure 5A:
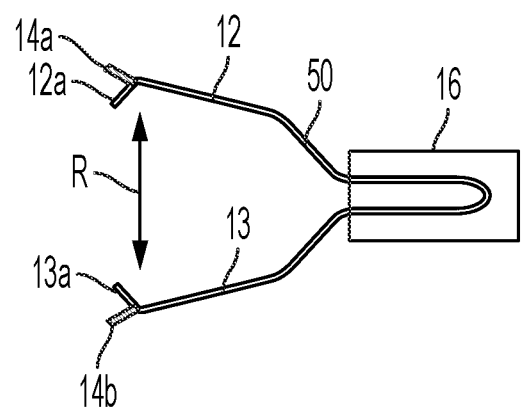
FIGS. 5A and 5B schematically illustrate a clip with anchors protruding from a first arm and second arm in directions divergent from the direction the first and second arms close. In this example, the clip forms a width (W) defined by opposite ends of the anchors when the clip is in a closed state, which is less than a width of a pressing tube or less than a width of a channel in a treatment tool.
Figure 5B:
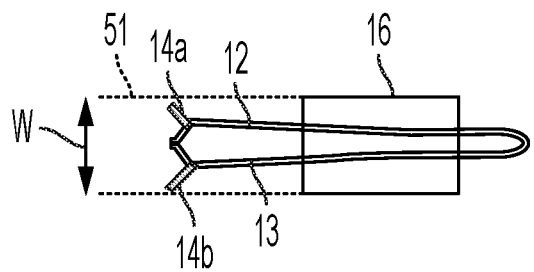

In separate embodiments, FIGS. 5A and 5B show clip 50 for gripping biological tissue of a patient having first arm 12, which has a first claw 12*a* at a distal end of the first arm 12 and a second arm 13, which has a second claw 13*a* at a distal end of the second arm 13. As further illustrated, first claw 12*a* and second claw 13*a* face each other and first arm 12 and second arm 13 are configured to move in a reciprocal direction (R) toward and away from each other to close and open the clip. As further illustrated in the figures, first arm 12 includes an anchor 14*a* protruding from the first arm 12 in a direction divergent from first claw 12*a* and a second arm 13 includes a second anchor 14*b* protruding from the second arm 13 in a direction divergent from second claw 13*a*. Clip 50 can deploy from within a pressing tube 16 to an open state (FIG. 5A). When in a closed state (FIG. 5B), the clip forms a width (W) defined by the distance between the distal ends of the anchors, which is less than a width of pressing tube 16 or less than a width of a channel in a treatment tool (51) such as a channel in an endoscope so that the anchors protruding from the arms (14*a*, 14*b*) do not contact or minimally contact the channel.

Figure 6A:
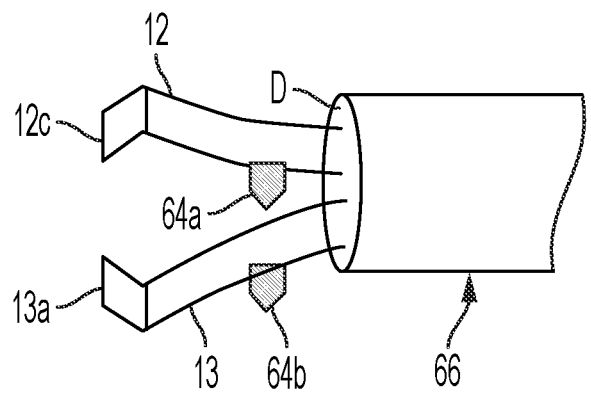
FIGS. 6A and 6B schematically illustrate a clip including anchors on arms protruding in a direction that is orthogonal to a plane formed by the arms and a pressing tube with an opening sufficiently large to allow the anchors to enter the tube when the clip is retracted in the pressing tube.
Figure 6B:
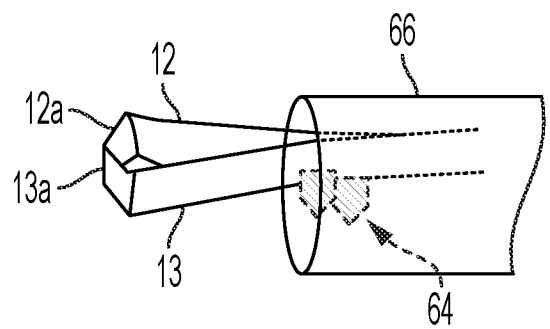

In another embodiment, FIGS. 6A and 6B show a clip having first arm 12, which has a first claw 12*a* at a distal end of the first arm 12 and a second arm 13, which has a second claw 13*a* at a distal end of the second arm 13. As further illustrated, first claw 12*a* and second claw 13*a* face each other and first arm 12 and second arm 13 are configured to move in a direct toward each other to close the clip. In this embodiment, claws 12a and 13a make contact when the arms are closed. As further illustrated in the figures, the clip includes an anchor 64a on first arm 12 and includes an anchor 64b on second arm 13 in which both anchors protrude in a direction that is orthogonal to a plane formed by first and second arm 12 and 13. Pressing tube 66 has an opening, e.g., diameter (D), sufficiently large to allow the anchors to enter the tube when the clip is retracted in the pressing tube. FIG. 6B shows the anchors 64 in pressing tube 66 when the clip is retracted in the pressing tube and the clip is in a closed state.

It should be noted that the arms, claws and anchors can have suitable forms, such as the form of a wire (as in the embodiments illustrated in, e.g., FIGS. 1A to 1D, or as the form of a ribbon (as in the embodiments illustrated in, e.g., FIGS. 6A and 6B), or can have a mixed form, such as one of the arms and claws in the form of a ribbon and the anchors in the form of a wire.

Figures 7A, 7B:
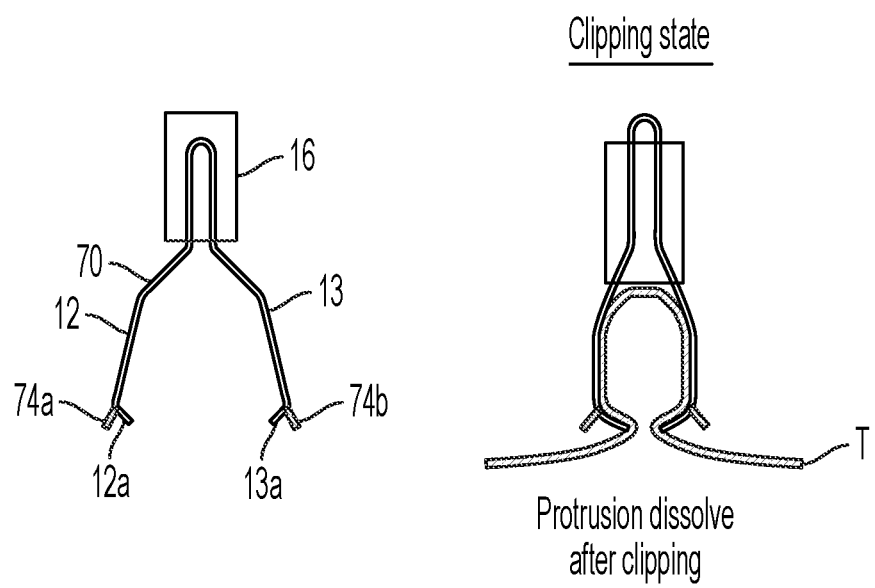
FIGS. 7A, 7B, 7C schematically illustrate a clip for gripping biological tissue of a patient having one or more anchors that are bioabsorbable in accordance with aspects of the present disclosure.
Figure 7C:
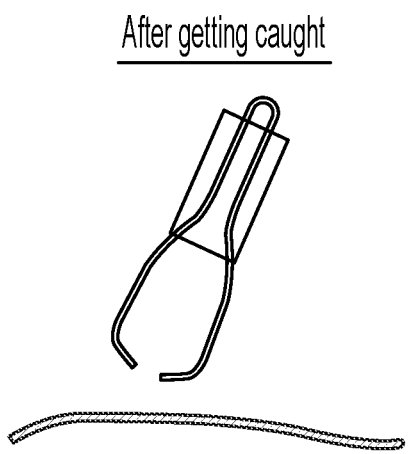

FIGS. 7 through 8 illustrate other aspects of anchors that can be included on arms of clips. In particular, FIGS. 7A-7C show clip 70 for gripping biological tissue (T) of a patient has a first arm 12, which has a first claw 12a at a distal end of the first arm 12 and a second arm 13, which has a second claw 13a at a distal end of the second arm 13. First claw 12a and second claw 13a face each other. As further illustrated, first arm 12 includes a first anchor 74a on an outer surface of first arm 12 protruding in a direction divergent from first claw 12a and a second arm 13 includes a second anchor 74b on an outer surface thereof protruding in a direction divergent from second claw 13a. In this example, first and second anchors, 74a and 74b, are made of a bioabsorbable material. In this way, after the anchors attach to the tissue (T), they can eventually dissolve in the tissue and be removed from the clip (FIG. 7C). Such anchors made of bioabsorbable can be initially attached to the clip arms by an adhesive, such as a bioabsorbable adhesive.

Figure 8A:
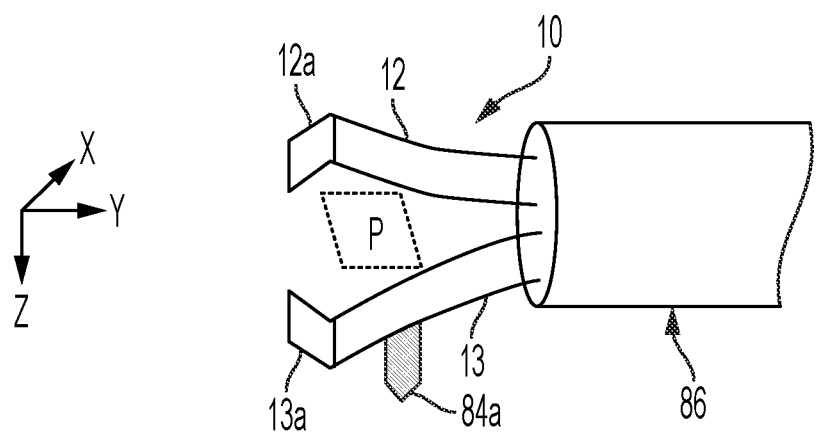
FIGS. 8A, 8B, 8C schematically illustrate a clip for gripping biological tissue of a patient having with one anchor in accordance with aspects of the present disclosure.
Figures 8B, 8C:
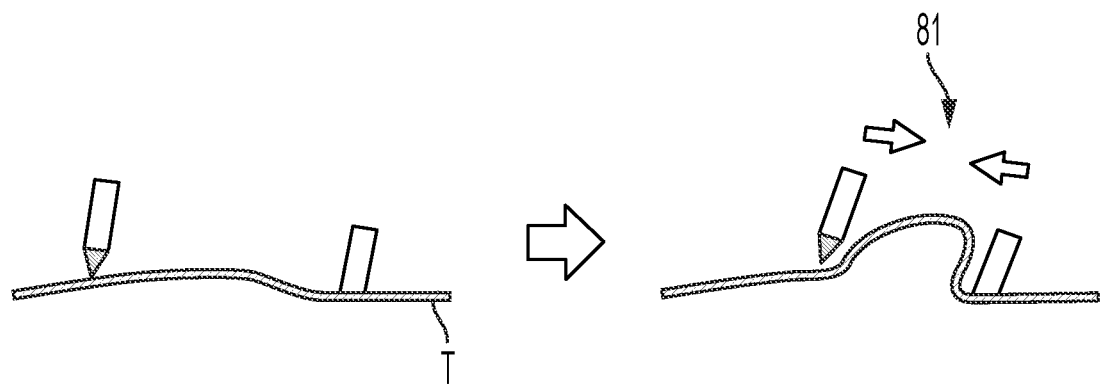
Figure 9A:
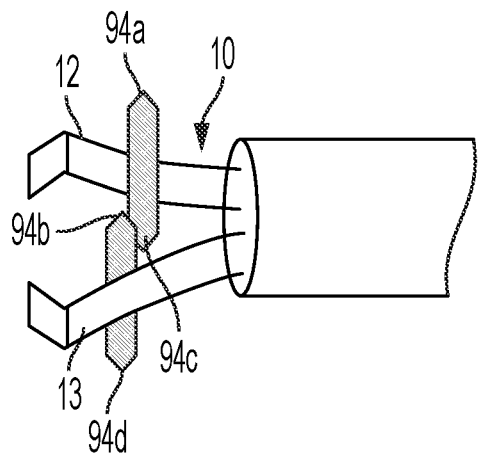
FIGS. 9A, 9B, 9C schematically illustrate clips having more than one anchor per arm, and/or in which anchors protrude in different directions from each other in accordance with aspects of the present disclosure.
Figure 9B:
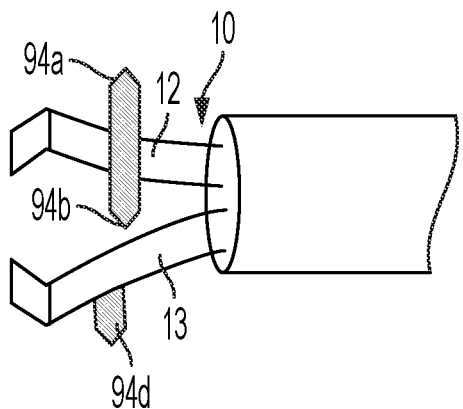
Figure 9C:
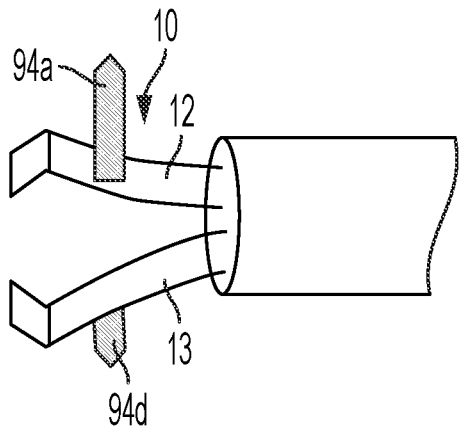
Figure 10A:
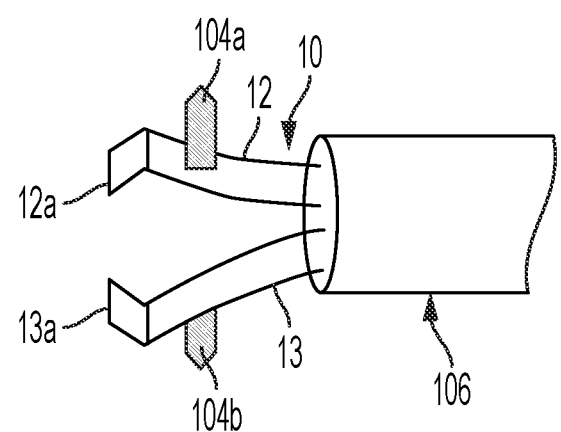
FIGS. 10A, 10B, 10C schematically illustrate a clip for gripping biological tissue of a patient having with two anchors in accordance with aspects of the present disclosure.
Figures 10B, 10C:
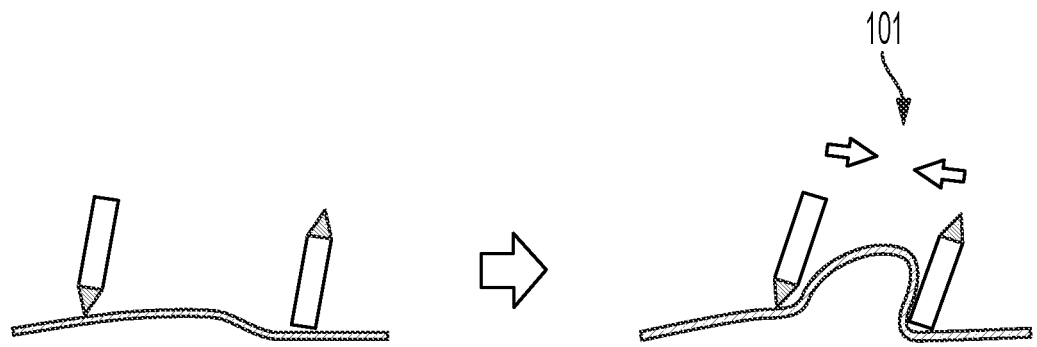

FIGS. 8-11 show anchors that protrude in a direction that is orthogonal to a plane defined by the first and second arm. In particular, FIGS. 8 and 10 show clip 10 for gripping biological tissue (T) of a patient including a first arm 12, which has a first claw 12a at a distal end of the first arm 12, and a second arm 13, which has a second claw 13a at a distal end of the second arm 13, in which first claw 12a and second claw 13a face each other and first arm 12 and second arm 13 are configured to move toward each other to close the clip. In FIG. 8A, first arm 12 includes a first anchor 84a in which the anchor protrude from the first arm in a direction that is orthogonal to a plane (P) defined by the first and second arm. As shown in the figure, the arms can form a plane with x and y coordinates and the anchor can protrude in the z coordinate. In FIG. 10A, first arm 12 includes a first anchor 104a in which the anchor protrude from the first arm in a direction that is orthogonal to a plane defined by the first and second arm and second arm 13 includes a second anchor 104b in which the anchor protrude from the second arm in a direction that is orthogonal to a plane defined by the first and second arm. Anchors 104a and 104b protrude in opposite directions from a plane defined by the arms. A configuration in which the anchor or anchors protrude in a direction that is orthogonal to a plane defined by the first and second arm advantageously can cause tissue caught by the orthogonal anchor (FIGS. 8B, 10B) to elevate when the arms approach each other (81, 101 in FIG. 8C, FIG. 10C, presectively) which facilitates grasping the tissue in the arms.

FIGS. 9A-9C illustrate clips having more than one anchor per arm, and/or in which anchors protrude in different directions from each other. In particular, FIG. 9A shows first arm 12 with two anchors. A first anchor 94a protrudes from first arm 12 in a direction that is orthogonal to a plane defined by the first and second arm, a second anchor 94c which protrudes from first arm 12 in a direction that is orthogonal to a plane defined by the first and second arm but opposite of first anchor 94a. Second arm 13 also has two anchors. A third anchor 94b protrudes from second arm 13 in a direction that is orthogonal to a plane defined by the first and second arm, a fourth anchor 94d which protrudes from second arm 13 in a direction that is orthogonal to a plane defined by the first and second arm but opposite of third anchor 94c. FIG. 9B shows first arm 12 with two anchors (94a, 94b) and second arm 13 with a third anchor (94d). FIG. 9C shows each of the arms of the clips having one anchor (94a, 94d) but the anchors protrude in opposite directions from a plane defined by the arms.

Figure 11A:
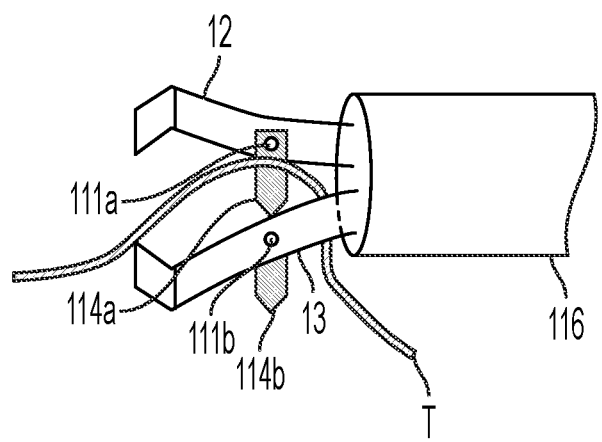
FIGS. 11A, 11B and 11C schematically illustrate a clip having anchors configured to rotate into the plane of the arms of the clip in accordance with aspects of the present disclosure.
Figure 11B:
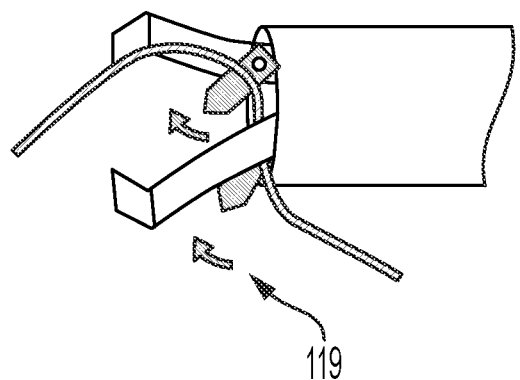
Figure 11C:
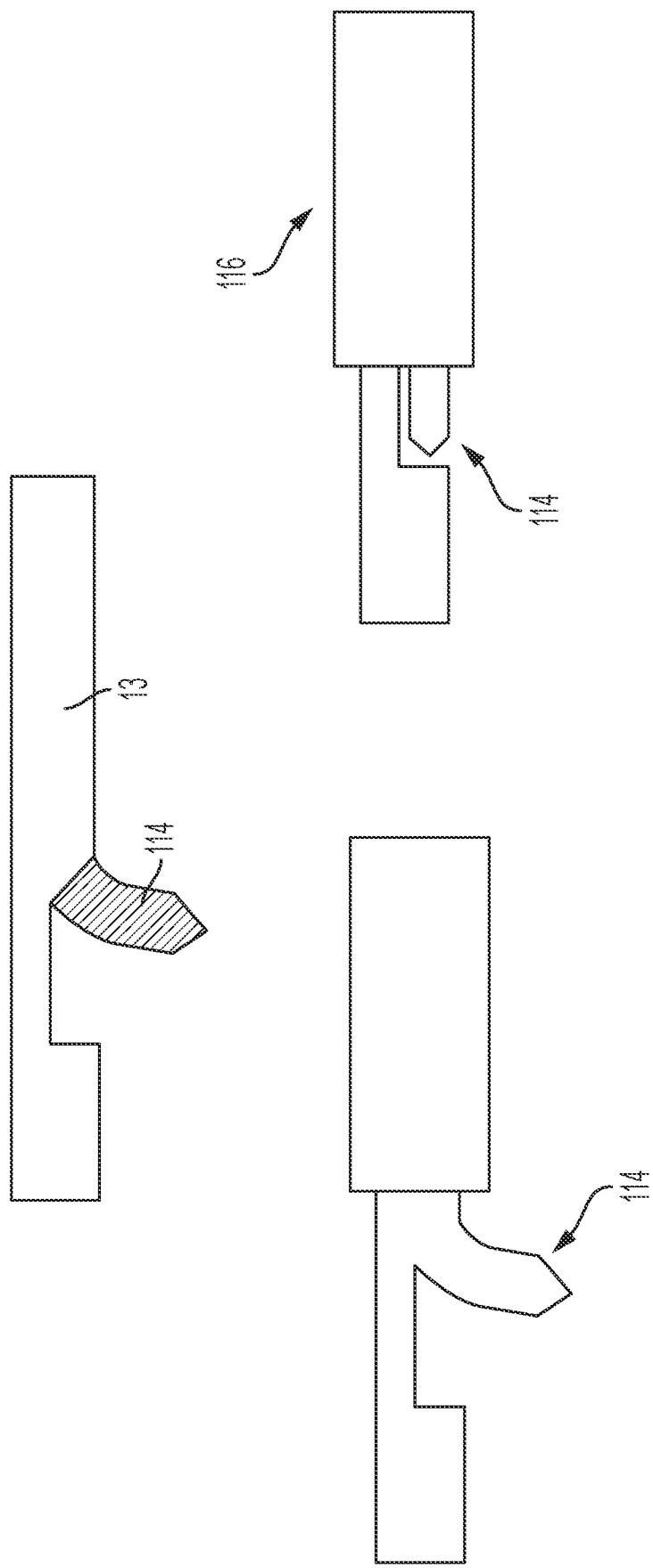

FIGS. 11A-11B and 11C illustrate anchors configured to rotate into the plane of the arms when the clip is retracted in a pressing tube. For example and with reference to FIGS. 11A-11B, first and second anchors (111a, 111b) are attached to their respective first and second arms (12, 13) by a structure, for example pins (111a, 111b), which allows the anchors to rotate (119) toward the plane defined by the arms when the clip is retracted into the pressing tube 116 and an edge of the pressing tube contacts the anchors.

FIG. 11C shows another structure configured to rotate the anchor into the plane of the arms of a clip when the arms are slidable retracted or extended from a pressing tube. As shown, anchor 114 is formed integral to clip arm 13 and biased in an open state but when retracted in pressing pipe 116 is in a closed state. By this structure, no pins are needed on the arms of the clips to include anchors which can rotate toward the plane defined by the arms when the clip is retracted into the pressing tube 116. Instead, the anchors have a spring open bias and pops-out of the pressing tube upon extended distally from the tube.

Figure 12A:
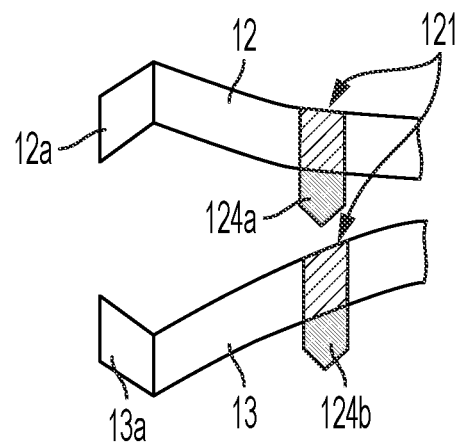
FIGS. 12A and 12B schematically illustrate a clip with arms having markers which identify the location of anchors on the respective arms in accordance with aspects of the present disclosure.
Figure 12B:
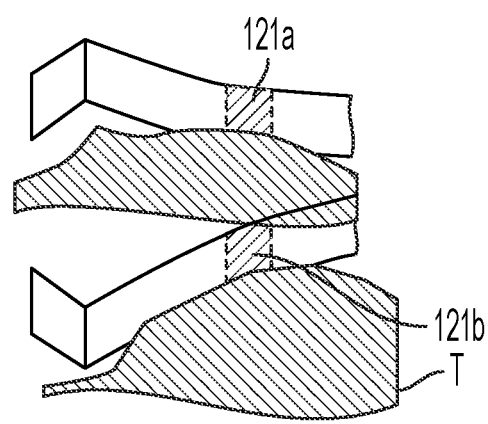
Figures 14A, 14B:
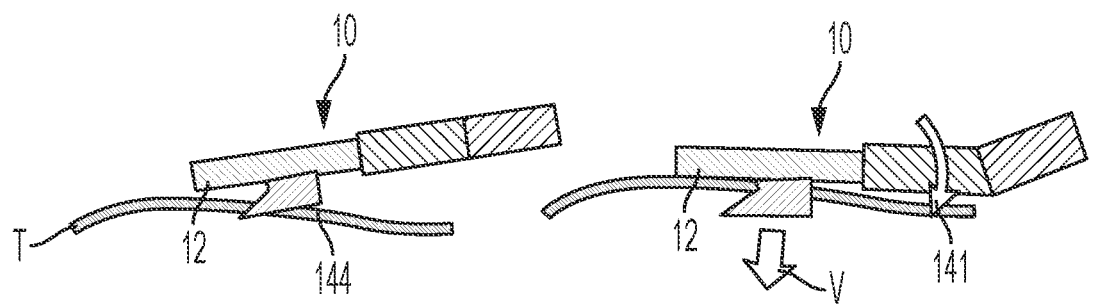
FIGS. 14A and 14B schematically illustrate a side view of a clip arm with an anchor protruding from the arm in a vertical direction from the longitudinal direction of the first arm. In this example, the anchor is in the shape of a hook, which allows the clip to be attached vertically on the tissue.

FIGS. 12-13 illustrate clips having anchors that can be more easily identified when the clips are is use. For example, FIGS. 12A and 12B show first arm 12 and second arm 13 with a marker 121 on the respective arms which identifies the location of first anchor 124a or 124b on the respective arms. In this way, when the anchors are not readily visible to a user such as when the anchors are caught in tissue (T), the user can identify the location of the anchors by the markers (121a, 121b) on the respective first or second arm. The markers 121 on the arms of the clip can be caused by a fluorescent marker, color, symbol, texture on the arm such as a roughness, etc. or equivalent on the arm at the location of the anchor.

FIGS. 13A and 13B illustrate clips with claws that have a gap or in which a width of a claw is greater or less than a width of the anchor so that the anchors can be more readily observed when the clip is in use. For example, FIGS. 13A-13B show clip 10 with first and second arms (12, 13) having first and second claws (12a, 13a) in which first and second anchors have a width that is smaller than the width of the claws (134a, 134b) or a width that is greater than the claws (134c, 134d) to facilitate observing the anchors when in use. In addition, or alternatively, the claws can include a gap to facility observing the anchors. FIG. 13A shows first claw 132a with a gap which facilitates observing anchor 134a and second claw 133a has a gap which facilitates observing anchor 134b.

FIGS. 14-20 schematically illustrate clip arms in accordance with the present disclosure that can further advantageously apply a vertical force to tissue when the clip is tangential thereto and can bend to facility placing multiple clips in close proximity to each other. For example, FIGS. 14A and 14B show a side view of clip 10 showing first arm 12 with anchor 144 protruding from the first arm 12 in a vertical direction from the longitudinal direction of the first arm. In this example, anchor 144 is in the shape of a hook and in a direction that is orthogonal to a plane defined by the first and second arm of the clip, which allows the clip to be placed vertically on the tissue. After anchor 144 attaches to tissue (T), the clip can be rotated 141 which results in a vertical force on the tissue. Another advantage of anchors on clips as set forth in the present disclosure is that such clips can be pressed firmly against the mucosa allowing more tissue to be inserted between the claws and more tissue grasped by the clip.

In certain embodiments, clips of the present disclosure can be disconnected from a surgical tool and clipped on tissue of a patient. To facilitate placing clips adjacent to each other, the clip arms can be configured to bend. A shown in the side views of FIGS. 15A and 15B, a clip can be configured to be released from a surgical tool after the clip is attached to tissue of a patent (150a). However, placement of a second clip (150b) is somewhat limited due to the proximal end of the clip and any member attached to the proximal end of the clip such as a pressing tube 156. In this example, clip 150c has a first arm 152 and second arm (not shown) with a first anchor 154 on first arm 152 and pressing tube 156. As shown, clip 150c includes a bending portion or member 151 along the clip. In this way, clips having anchors and arms configured to bend (150c and 150d) can be more readily placed adjacent to one another when attached to tissue of a patient.

FIGS. 16-20 schematically illustrate various structural features which configure a clip arm to bend. For example, FIGS. 16A and 16C show clip 160 having a first arm 162 which includes a member 161 with high elasticity. The second arm of clip 162 would also have a member with high elasticity, but is not illustrates in the side view of FIG. 16. The clip arms are bias to be in a bent state such that when the clip is loaded in pressing tube 166, the clip arms are in a straight position (L), but when deployed from pressing tube 166, clip arm 162 bends as shown in the unloaded state (U). As an alternative, or in addition to, an elastic member, a clip arms can have one or more springs to bias the clip arms in a bent state. When such a clip is placed in a channel of an endoscope (165), the arms would be in a straight state but when deployed from the channel, the arms would bend (FIG. 16B). In FIG. 17A, clip arm 172 includes a notch 171 which can relieve stress when the arm is bent.

Figure 19A:
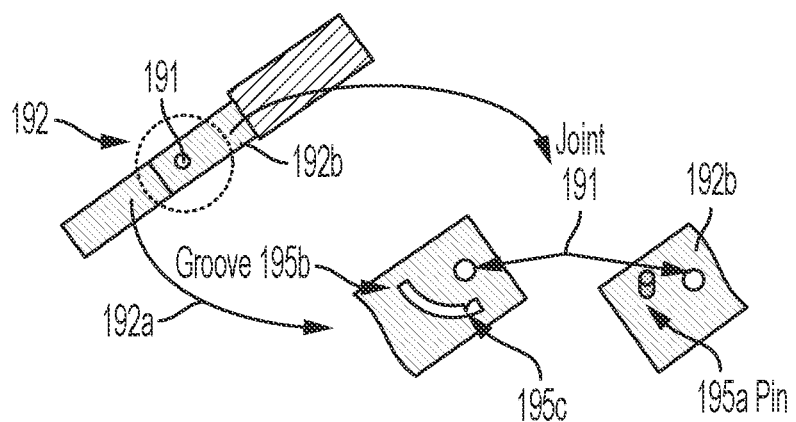
FIGS. 19A and 19B schematically illustrate a clip with arms having two part articulated together through joints in which the arms can lock in a bent state in accordance with aspects of the present disclosure.
Figures 19B, 19C:
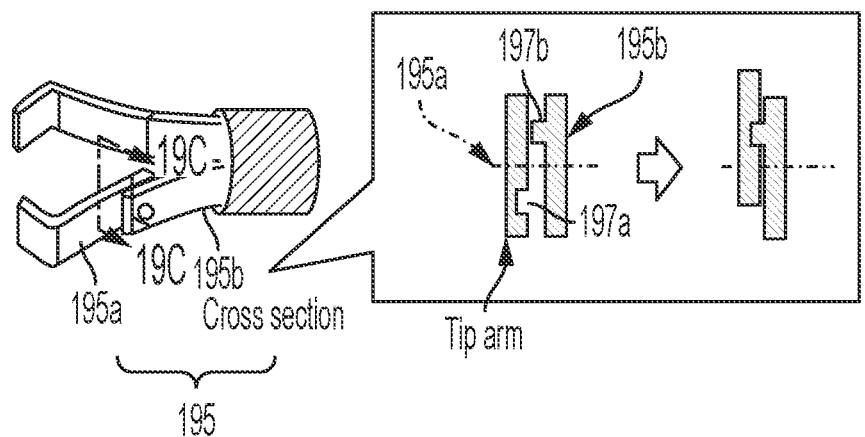
FIG. 19C is an enlarged view of an arm of a clip of FIG. 19B.

Other structures that could be used to configure the arms of clips of the represent disclosure to bend are illustrated in FIGS. 18-20. In FIGS. 18A and 18B, clip arm 182 includes two part (182a, 182b) articulated together through joint 181. FIGS. 19A-19C illustrate locking configurations of an arm of a clip configured to bend. FIG. 19A shows clip arm 192 comprised of two articulating parts (192a, 192b) connected by a joint 191. Part 192b can have a pin 195a that moves along a grove 195b when the arm is moving to a bent position. The pin can pass over a projection 195c in the grove 195b to lock the arm in the bent state. FIGS. 19B-19C show clip arm 195 comprised of two articulating parts (195a, 195b) connected by a joint 191 in which the inner part 195a of arm 195 has a concavity 197a and the outer part 195b of arm 195 has a convexity 197b such that when the outer part 195b of arm 195 rotates to position the arm in a bend state the concavity 197a fits in convexity 197b as shown in the cross sectional view of arm 195.

FIGS. 20A-20D illustrate clip arms articulated together through springs. In FIG. 20A, arm 202 includes two parts (202a, 202b) connected together by a spring 201. The clip arm is bias to be in a bent state such that when the clip is loaded in pressing tube 206, the clip arm is in a straight position (L), but when deployed from pressing tube 206, clip arm 202 bends as shown in the unloaded state (U) in FIG. 20A. When such a clip is placed in a channel of an endoscope (205), the arms of the clip would be in a straight state (FIG. 20C) but when deployed from the channel, the arms would bend (FIGS. 20A and 20D).

In other examples, the clip arms can be made of a shape memory alloy, such as Nitinol, and are in the straightened or bent configuration based on stress state or temperature.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A clip, comprising:
   a first arm, the first arm including:
      a first elongated body having a distal end,
      a first claw located at the distal end of the first elongated body, and
      an anchor located at the distal end of the first arm; and
   a second arm, the second arm including:
      a second elongated body having a distal end, and
      a second claw located at the distal end of the second elongated body,
   wherein the first arm is movable relative to the second arm in an operational plane between an open position and a closed position,
   wherein the first claw protrudes from the distal end of the first elongated body toward the second arm,
   wherein the second claw protrudes from the distal end of the second elongated body toward the first arm,
   wherein the anchor has a first state and a second state and, in the first state, the anchor extends from the first elongated body in a first direction that intersects the operational plane and, in the second state, the anchor extends from the first elongated body in a second direction different from the first direction, and
   wherein the first elongated body has a cutout and an entirety of the anchor is located within the cutout when the anchor is in the second state.

2. The clip of claim 1, wherein the first elongated body and the anchor are integrally formed.

3. The clip of claim 1, wherein a distal end of the anchor is located within a width of a part of the first elongated body when the anchor is in the second state, the width of the first elongated body is a length in the first direction.

4. The clip of claim 3, wherein an entirety of the anchor is located within the width of the first elongated body when the first anchor is in the second state.

5. The clip of claim 1, wherein the anchor is configured to change between the first state and the second state by elastic deformation of the anchor.

6. The clip of claim 1, wherein a bottom surface of the anchor is on an extension line of a bottom surface of the first elongated body when the anchor is in the second state.

7. The clip of claim 1, further comprising a tube,
wherein the tube is configured to move between a first position and a second position,
wherein, in the first position, an entirety of the anchor is out of the tube and, in the second position, a part of the anchor is in the tube, and
wherein the anchor is in the first state when the tube is located in the first position.

8. The clip of claim 7, wherein a distal end of the anchor is located radially outward from an outer peripheral surface of the tube when the anchor is in the first state.

9. The clip of claim 7, wherein the anchor is in the second state when the tube is located in the second position.

10. The clip of claim 1, wherein the first elongated body has a first side and a second side opposite to the first side, the first side extending along a longitudinal direction of the clip,
wherein the anchor is a single anchor extending from the first side, and
wherein the first arm has only the single anchor.

11. The clip of claim 1, wherein the first elongated body has a first side and a second side opposite to the first side, the first side extending along a longitudinal direction of the clip,
wherein the anchor extends from the first side, and
wherein no anchor extends from the second side.

12. The clip of claim 1, wherein the first elongated body has a first side and a second side opposite to the first side, the first side extending along the operational plane,
wherein the anchor is a single anchor extending from the first side, and
wherein the first arm has only the single anchor.

13. The clip of claim 1, wherein the first elongated body has a first side and a second side opposite to the first side, the first side extending along the operational plane,
wherein the anchor is extended from the first side, and
wherein no anchor is extended from the second side.

14. The clip of claim 1, wherein the anchor is located proximally relative to the distal end of the first elongated body.

15. The clip of claim 1, wherein the first elongated body has a first side and a second side opposite to the first side, the first side and the second side extending along the operational plane, and
wherein the first elongated body has the cutout on the first side.

16. The clip of claim 1, wherein the first elongated body has a first side and a second side opposite to the first side, the first side extending along the operational plane.

17. The clip of claim 1, wherein the first direction is orthogonal to the operation plane.

18. The clip of claim 1, wherein the second direction is parallel to the operational plane.

19. A clip device, comprising:
the clip of claim 1; and
a tube,
wherein a part of the clip is exposed from the tube when the anchor is in the first state, and
wherein the part of the clip is retracted into the tube when the anchor is in the second state.

* * * * *